United States Patent
Berndt (10) Patent No.: US 8,438,910 B2
(45) Date of Patent: May 14, 2013

(54) SHEAR VALVE WITH DLC COMPRISING MULTI-LAYER COATED MEMBER

(75) Inventor: Manfred Berndt, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 379 days.

(21) Appl. No.: 12/755,804

(22) Filed: Apr. 7, 2010

(65) Prior Publication Data

US 2010/0281959 A1    Nov. 11, 2010

(30) Foreign Application Priority Data

May 7, 2009   (EP) .................................. 09159695

(51) Int. Cl.
*G01N 30/36*   (2006.01)

(52) U.S. Cl.
USPC ........................................................ 73/61.56

(58) Field of Classification Search ................. 73/61.56; 137/625.46

See application file for complete search history.

(56) References Cited

U.S. PATENT DOCUMENTS

| | | | |
|---|---|---|---|
| 4,068,528 A | | 1/1978 | Gundelfinger ............. 73/864.84 |
| 4,824,262 A | * | 4/1989 | Kamigaito et al. ............. 384/42 |
| 5,093,647 A | * | 3/1992 | Noda et al. ..................... 338/160 |
| 2003/0098076 A1 | | 5/2003 | Nichols ....................... 137/625.4 |
| 2006/0147631 A1 | * | 7/2006 | Lev et al. ........................ 427/290 |
| 2011/0315633 A1 | * | 12/2011 | Cormier et al. ................ 210/656 |

FOREIGN PATENT DOCUMENTS

| | | |
|---|---|---|
| EP | 0321774 | 6/1989 |
| EP | 1520837 | 4/2005 |
| WO | 03/074898 | 9/2003 |
| WO | 2006/056236 | 6/2006 |
| WO | 2009/003519 | 1/2009 |

OTHER PUBLICATIONS www.busmi.com/files/N709DE.pdf.
http://www.17-4ph.co.uk/.
http://www.idexhs.com/products/Default.aspx?ProductID=3295.
http://idexhs.com/support/rheodyne/tech_tips_01.aspx.
http://en.wikipedia.org/wiki/Column_chromatography.

* cited by examiner

*Primary Examiner* — Peter Macchiarolo
*Assistant Examiner* — Tamiko Bellamy (57) ABSTRACT

A shear valve for use in a high performance liquid chromatography system, the shear valve comprising a first shear valve member and a second shear valve member, wherein at least one of the first and second shear valve members is adapted to be moved with respect to the other, one of the first and second shear valve members comprises a plurality of ports, and the other comprises at least one fluid path for fluidly coupling respective ones of the ports in dependency on a relative movement position of the first and second shear valve members with respect to each other, wherein the first shear valve member is at least partially coated with an adhesion-promoting layer and a diamond like carbon layer on the adhesion-promoting layer.

19 Claims, 4 Drawing Sheets

SHEAR VALVE WITH DLC COMPRISING MULTI-LAYER COATED MEMBER

This application claims priority from European Patent Application, No. EP09159695.7 filed on 7 May 2009, which is incorporated by reference in its entirety.

BACKGROUND ART

The present invention relates to shear valves, in particular in a high performance liquid chromatography application.

In high performance liquid chromatography (HPLC, see e.g. http://en.wikipedia.org/wiki/HPLC), a liquid has to be provided usually at a very controlled flow rate (e.g. in the range of microliters to milliliters per minute) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid with compounds to be separated is driven through a stationary phase (such as a chromatographic column), thus separating different compounds of the sample fluid.

Valves are commonly used in HPLC applications, e.g. injection valves for injecting a liquid sample into a high pressure flowing stream of liquid, a purge valves for positive displacement pumps, flow path switching valves, etc. Such valves used in HPLC applications are often multi-position rotary valve. Examples of multi-position rotary valve are disclosed in U.S. Pat. No. 4,068,528 A (two-position valves) or US 2003/0098076 A1 (multi-function rotary valves or random-access, dual, three-way, rotary switching valves).

Shear valves, which can be used in multi-way embodiments, are usually formed by a housing and a body defining a stepped cavity in which the rotor or seal is positioned. The housing contains at least two shear seal valve members positioned to be aligned with ports in the rotor (body) to establish communication between the shear seal means. Shear valves are usually provided as rotary valves (such as the aforementioned rotary valves) or translational valves (often also called sliding valves), such as disclosed in EP 0321774 A2.

A multi-way switching valve allows for selectively routing a fluid input flow to the valve to one of more alternate output flows from the valve. A rotary valve is of the type wherein fluid flow is directed by rotating a valve rotor element to discrete angular positions relative to a stationary valve stator element. A dual rotary valve provides two valves in one valve body, both simultaneously operated by the positioning of the valve rotor. Rotary switching valves are commonly used, for example, in HPLC and other analytical methods to selectively direct a flow stream of one or more fluids along alternate paths to an analytical device or containment vessel.

The aforementioned US 2003/0098076 A1 shows in its FIG. 1 a conventional type of dual, three-way, switching valve 220, which includes a disc-shaped rotor with a set of rotor grooves in the front face of the rotor that contacts, in a fluid-tight manner, the face of a cylindrically shaped stator body at a rotor-stator interface. Inlet passages and outlet passages, longitudinally bored through the stator body to the rotor-stator interface, are selectively fluidly coupled through the rotor grooves corresponding to the rotation of the rotor relative to the stator. Pivoting of the rotor enables the rotor grooves to fluidly couple selected passages of the stator, depending on their placement on the rotor and the angular position of the valve rotor. Model 7030 of Rheodyne, L. P. is an example of this type of switching valve.

WO 2006/056236 A1, EP 1520837 A1, and PCT/EP07/056735, all by the same applicant, show other types or embodiments of valves used in HPLC.

In the aforementioned documents, the stator of the valves is typically made of metal and might comprise a stator seal (surfacing towards the rotor) made of a plastic-type material, such as an inert fluoropolymer, which is chemically inert, does not react with either the solvent or samples. In one embodiment of the U.S. Pat. No. 4,068,528 A, both the stator seal and a rotor seal (surfacing towards the stator) are formed of glass reinforced Tefzel with a chemical inertness approximately that of Teflon and glass and of sufficient mechanical strength to withstand high pressure, e.g., 50 MPa (7000 psi).

WO 03/074898 A1 relates to metal-ceramic composites for tribological uses and defined pairs based on such material. The friction heat generated between both sliding pairs and friction pairs has to be swiftly dissipated in order to maintain a lubricant film or ensure constant coefficients of friction. The document discloses metal-ceramic composites for friction/sliding uses, with basic compositions containing 30 to 75 percent by volume of one or several metallic phases, preferably aluminum and the alloys thereof, and 25 to 70 percent by volume of one or several non-metallic inorganic component/s as ceramic materials, preferably silicon carbide, aluminum oxide, titanium oxide, and silicates.

In modern HPLC with pressures rising up to 100 MPa and beyond, life time of valves becomes critical, in particular for the injection valve, as higher load on the rotor is required, which causes excessive wear.

DISCLOSURE

It is an object of the invention to provide an improved valve, in particular for high pressure HPLC applications. The object is solved by the independent claims. Further embodiments are shown by the dependent claims.

According to an embodiment of the present invention, a shear valve for use in a high performance liquid chromatography (HPLC) system is provided, the shear valve comprising a first shear valve member and a second shear valve member, wherein at least one of the first and second shear valve members is adapted to be moved with respect to the other, one of the first and second shear valve members comprises a plurality of ports, and the other comprises at least one fluid path for fluidly coupling respective ones of the ports in dependency on a relative movement position of the first and second shear valve members with respect to each other, wherein the first shear valve member is at least partially coated with an adhesion-promoting layer (such as titanium nitride, TiN) and a diamond like carbon (DLC) layer on the adhesion-promoting layer.

According to another embodiment of the present invention, a sample injector adapted to introduce a sample fluid into a mobile phase is provided, wherein the mobile phase is to be driven by a mobile phase drive through a separation unit for separating compounds of the sample fluid in the mobile phase, the sample injector comprising a sample loop for receiving the sample fluid and a shear valve having the above mentioned features for switching the sample loop between the mobile phase drive and the separation unit.

According to still another embodiment of the present invention, a fluid separation system for separating compounds of a sample fluid in a mobile phase is provided, the fluid separation system comprising a mobile phase drive, particularly a pumping system, adapted to drive the mobile phase through the fluid separation system, a separation unit, particularly a chromatographic column, adapted for separating compounds of the sample fluid in the mobile phase, and a shear valve having the above mentioned features for switching from one flow path to another flow path within a fluid separation flow path between the mobile phase drive and the separation unit.

According to yet another embodiment of the present invention, a method of manufacturing a shear valve for use in a high performance liquid chromatography system is provided, the method comprising assembling a first shear valve member and a second shear valve member so that at least one of the first and second shear valve members is adapted to be movable with respect to the other, one of the first and second shear valve members comprises a plurality of ports, and the other comprises at least one fluid path for fluidly coupling respective ones of the ports in dependency on a relative movement position of the first and second shear valve members with respect to each other, and at least partially coating the first shear valve member with an adhesion-promoting layer and a diamond like carbon layer on the adhesion-promoting layer.

The term "diamond like carbon" (DLC) may particularly denote one of different forms of amorphous carbon materials that display some of the unique properties of natural diamond but which have a different lattice structure. DLC may contain a significant amount of $sp^3$ hybridized carbon atoms. There are different types of DLC, wherein mixing these polytypes in various ways at the nanoscale level of structure, DLC coatings can be made that at the same time are amorphous, flexible, and yet purely $sp^3$ bonded "diamond". The hardest, strongest, and slickest is such a mixture, known as tetrahedral amorphous carbon, or ta—C. DLC can be used as a metal coating that is very scratch resistant and corrosion resistant. This type of coating is extremely hard and is surprisingly particularly appropriate from a tribological point of view to allow for a low friction contact with a corresponding friction partner.

The term "adhesion-promoting layer" may particularly denote a physical structure which may be sandwiched between a diamond like carbon structure on the one hand and a solid or bulk substrate on the other hand and which promotes adhesion of the DLC structure on the substrate. Such an adhesion-promoting layer may therefore safely prevent delamination of the DLC layer from the lower lying substrate.

According to an exemplary embodiment, two shear valve members may be arranged to properly cooperate as a tribological pair which can be moved with respect to one another basically without abrasion and in a low frictional manner. This can particularly be achieved by providing a stack of an adhesion-promoting layer synergetically combined with a diamond like carbon layer, the adhesion-promoting layer being sandwiched between the DLC and the lower lying substrate of at least one of the shear valve members. By taking this measure, undesired delamination of the DLC layer from the substrate may be safely prevented even in a scenario in which high friction forces act as a consequence of a relative motion of the contacting shear valve members to one another. Therefore, the lifetime of the shear valve may be significantly increased by the stack-like coating comprising DLC in combination with an adhesion-promoting layer.

In the following, further exemplary embodiments of the shear valve will be explained. However, these embodiments also apply to the sample injector, the fluid separation system, and the method.

In an embodiment, an ion implantation layer may be formed on and/or in the diamond like carbon layer. The term "ion implantation layer" may particularly denote a layer which is formed by implanting ions, for instance electrically charged particles, atoms or molecules, on or in an exposed surface of the DLC layer. It is believed that the provision of near-surface or on-surface particles introduced by ion implantation into or onto a DLC layer may significantly reduce frictional wear between a tribological pair of moving partner members. For example, carbon, molybdenum disulfide ($MoS_2$), titanium, titanium dioxide ($TiO_2$) or boronitride have turned out to be appropriate ion implantation materials.

In an embodiment, the first shear valve member may comprise a first solid body on which the adhesion-promoting layer and the diamond like carbon layer are arranged. This first solid body may comprise steel (particularly stainless steel, duplex steel, super duplex steel, steel with a manganese contribution of at least 3%, particularly of at least 5%, steel with a nickel contribution of less than 8%, particularly of less than or equal to 5%) or any other suitable electrically conductive material. Steel materials, particularly hardened steel versions as the ones mentioned above, have turned out to be particularly appropriate as a bulk material of the first solid body because of the high robustness of such materials. Electrically conductive materials have the further advantage that a voltage can be applied to such materials, for instance when forming individual layers on the first shear valve by a galvanic method. In case of a plasma treatment for forming specific layers, particularly an ion implantation layer, it is also possible to use an electrically insulating material for the solid body.

The second shear valve member may be at least partially coated with a further adhesion-promoting layer and a further diamond like carbon layer on the further adhesion-promoting layer. In such an embodiment, both shear valve members serving as tribological partner members may be covered with a stack of DLC and an adhesion-promoting layer, for instance with the same stack. By taking this measure, the tribological cooperation of these members may be further improved.

Still referring to the previous embodiment, the second shear valve member may comprise a second solid body on which the further adhesion-promoting layer and the further diamond like carbon layer are arranged. This second solid body may comprise steel (particularly stainless steel, duplex steel, super duplex steel, steel with a manganese contribution of at least 3%, particularly of at least 5%, steel with a nickel contribution of less than 8%, particularly of less than or equal to 5%) or any electrically conductive material.

For instance, any one of the solid body of the first and the second shear valve member may comprise 1.4534 X3CrNiMo A113-8-2 (compare www.busmi.com/files/N709DE.pdf), 1.4574 or Allegheny Ludlum AL 15-7 High Strength Stainless Steel, UNS S15700, 1.4542 X5CrNiCuNb16.4 (compare http://www.17-4ph.co.uk/), etc. These steel configurations have a particularly high basic hardness which may have a positive impact on the protection with respect to cavitation effects. The effect of cavitation may exert a high mechanical impact on the shear valve members when a strong pressure pulse impacts the shear valve which may happen in a HPLC when switching between an operation mode in which a sample loop is switched in or out of fluid communication with a mobile phase drive such as a high pressure pump, for instance is switched between a high pressure of 1000 bar and an atmospheric pressure.

The second shear valve member may comprise a second solid body on which a further ion implantation layer may be arranged. Particularly in a scenario in which the second shear valve member has also an ion implantation (which may be made of carbon, molybdenum disulfide, titanium, or titanium oxide, etc.) the second solid body may comprise a polymer material (such as polyimide, polyamideimide, polyetheretherketone, PEEK, a PEEK Blend T-Series, a PEEK/PBI/

PTFE Blend, a PEEK-HT/PBI/Carbon/PTFE Blend, a PEEK-HT/PBI/Carbon/TIO$_2$/PTFE Blend), a metal material or a ceramics material.

In an embodiment, the fluid path which may be provided in one of the shear valve members may comprise one or more grooves. Hence, one or more oblong recesses or indentations may be provided within such a shear valve member allowing a fluid to flow through such a groove. The groove may be an oblong, slightly curved fluidic channel.

In an embodiment, the groove may comprise an insert, such as a ceramic insert which may be molded, and may have at least a part of the diamond like carbon layer and the adhesion-promoting layer covering at least a part of a surface within the groove. By taking this measure, the cavitation effect acting on a conventional shear valve for HPLC applications may be significantly reduced, thereby protecting the shear valve against abrasion during such switches. During such a switch, particularly the small grooves in the shear valve are prone to be negatively impacted by a sudden change of the pressure conditions.

In an embodiment, the diamond like carbon layer may have a thickness in a range between about 0.2 µm and about 3 µm, particularly in a range between about 0.5 µm and about 2 µm. These thicknesses have turned out to be particularly appropriate to obtain a high hardness and desired tribological effects in combination with the safe protection against undesired delamination of a DLC layer accomplished by the adhesion-promoting layer.

The adhesion-promoting layer may have a thickness in a range between about 1 µm and about 5 µm, particularly between about 2 µm and about 4 µm. Particularly in combination with the aforementioned thicknesses of the DLC layer, these thicknesses of the adhesion-promoting layer have turned out to be particularly appropriate to enable a safe adhesion of the DLC layer on the lower lying solid substrate. At least a part of the diamond like carbon layer and the adhesion-promoting layer may cover at least a part of a surface within one or more of the ports. Therefore, undesired cavitation effects may be further suppressed by covering the surfaces of the ports with a hard layer protecting the ports against undesired impacts due to pressure drops or the like.

In one embodiment, the shear valve is embodied as a rotary valve, with the first and second shear valve members being rotably moveable with respect to each other. In another embodiment, the shear valve is embodied as a translational valve, such as a slide valve, with the first and second shear valve members being translationally moveable with respect to each other.

The second shear valve member is preferably at least partially coated with or comprised of a material tribologically matching to the first shear valve member material.

In one embodiment, the shear valve further comprises a housing for housing one of the first and second shear valve members, wherein the housing is pre-stressed (pre-loaded) against the housed shear valve member. This allows reducing breakage or fracture stress, which may occur in the housed shear valve member, in particular in case and as more such shear valve member comprises a ceramic material. The housing is preferably attached to the housed shear valve member by using a shrinking process as known in the art.

Preferably, the first shear valve member is the housed shear valve, thus allowing to frame the ceramic or partial ceramic member and reducing tension.

The housing can be made of or comprise a stainless steel, which might be coated with diamond like carbon (DLC), optionally in combination with an adhesion promoting layer, etc.

In one embodiment, one or more of the ports of the shear valve comprises a through hole having an opening fluidly coupling with the fluid path dependent on the moving position.

In one embodiment, wherein the first shear valve member comprises a plurality of ports, the second shear valve member comprises the at least one fluid path for fluidly coupling respective ones of the port independency on a relative movement position of the first and second shear valve member with respect to each other.

In a further embodiment, the second shear valve member is adapted to be moved with respect to the first shear valve member. Preferably, the second shear valve member is provided as rotor or slider moving on the first shear valve member, which is embodied as static member and not moving.

A drive might be provided for moving the shear valve member to be moved. Alternatively or in addition, the shear valve member to be moved might also be moved manually.

A valve control unit, such as an excenter, might be provided for controlling movement of the shear valve member to be moved.

The shear valve is preferably adapted to conduct a liquid in the at least one fluid path at a high pressure at which compressibility of the liquid becomes noticeable, such as pressure in the range of 20-200 MPa, and particularly 50-120 MPa.

The shear valve can be a sample injection valve for injecting a liquid sample into a high pressure flowing stream of liquid, a high pressure purge valve for a positive displacement pump, or a flow path switching valve for switching from one flow path to another flow path.

The shear valve might be embodied in an HPLC sample injector adapted to introduce a sample fluid into a mobile phase. The mobile phase is to be driven by a mobile phase drive through a separation unit for separating compounds of the sample fluid in the mobile phase. A sample loop is provided for receiving the sample fluid. The shear valve is provided for switching the sample loop between the mobile phase drive and the separation unit for introducing the sample fluid into the mobile phase.

Embodiments of the present invention might be embodied based on most conventionally available HPLC systems, such as the Agilent 1200 Series Rapid Resolution LC system or the Agilent 1100 HPLC series (both provided by the applicant Agilent Technologies—see www.agilent.com—which shall be incorporated herein by reference).

One embodiment comprises a pumping apparatus having a piston for reciprocation in a pump working chamber to compress liquid in the pump working chamber to a high pressure at which compressibility of the liquid becomes noticeable.

One embodiment comprises two pumping apparatuses coupled either in a serial or parallel manner. In the serial manner, as disclosed in EP 309596 A1, an outlet of the first pumping apparatus is coupled to an inlet of the second pumping apparatus, and an outlet of the second pumping apparatus provides an outlet of the pump. In the parallel manner, an inlet of the first pumping apparatus is coupled to an inlet of the second pumping apparatus, and an outlet of the first pumping apparatus is coupled to an outlet of the second pumping apparatus, thus providing an outlet of the pump. In either case, a liquid outlet of the first pumping apparatus is phase shifted, preferably essentially 180 degrees, with respect to a liquid outlet of the second pumping apparatus, so that only one pumping apparatus is supplying into the system while the other is intaking liquid (e.g. from the supply), thus allowing to provide a continuous flow at the output, However, it is clear that also both pumping apparatuses might be operated in parallel (i.e. concurrently), at least during certain transitional phases e.g. to provide a smooth(er) transition of the pumping cycles between the pumping apparatuses. The phase shifting might be varied in order to compensate pulsation in the flow of liquid as resulting from the compressibility of the liquid. It is also known to use three piston pumps having about 120 degrees phase shift.

The separating device preferably comprises a chromatographic column (see e.g. http://en.wikipedia.org/wiki/Column chromatography) providing the stationary phase. The column might be a glass or steel tube (e.g. with a diameter from 50 µm to 5 mm and a length of 1 cm to 1 m) or a microfluidic column (as disclosed e.g. in EP 1577012 or the Agilent 1200 Series HPLC-Chip/MS System provided by the applicant Agilent Technologies, see e.g. http://vvvvw.chem.agilent.com/Scripts/PDS.asp?1Page=38308). For example, a slurry can be prepared with a powder of the stationary phase and then poured and pressed into the column. The individual components are retained by the stationary phase differently and separate from each other while they are propagating at different speeds through the column with the eluent. At the end of the column they elute one at a time. During the entire chromatography process the eluent might be also collected in a series of fractions. The stationary phase or adsorbent in column chromatography usually is a solid material. The most common stationary phase for column chromatography is silica gel, followed by alumina. Cellulose powder has often been used in the past. Also possible are ion exchange chromatography, reversed-phase chromatography (RP), affinity chromatography or expanded bed adsorption (EBA). The stationary phases are usually finely ground powders or gels and/or are microporous for an increased surface, though in EBA a fluidized bed is used.

The mobile phase (or eluent) can be either a pure solvent or a mixture of different solvents. It can be chosen e.g. to minimize the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic is delivered in separate bottles, from which the gradient pump delivers a programmed blend to the system. Other commonly used solvents may be isopropanol, THF, hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The pressure in the mobile phase might range from 2-200 MPa (20 to 2000 bar), in particular 10-150 MPa (100 to 1500 bar), and more particular 50-120 MPa (500 to 1200 bar).

The HPLC system might further comprise a sampling unit for introducing the sample fluid into the mobile phase stream, a detector for detecting separated compounds of the sample fluid, a fractionating unit for outputting separated compounds of the sample fluid, or any combination thereof. Further details of HPLC system are disclosed with respect to the Agilent 1200 Series Rapid Resolution LC system or the Agilent 1100 HPLC series, both provided by the applicant Agilent Technologies, under www.agilent.com which shall be in cooperated herein by reference.

Coatings according to exemplary embodiments may be applied to shear valve members from the company Rheodyne (compare http://www.idex-hs.com/products/Brand.aspx?BrandID=8, http://www.idex-hs.com/products/Defaul-t.aspx?ProductID=3295, http://www.idex-hs.com/support/rheodyne/tech tips 01.aspx, etc.).

Exemplary embodiments specifically address to the problem of a high mechanical load acting on a fluidic valve upon operation of this valve, particularly in the field of HPLC. When switching a high pressure pump (which may operate at 1000 bar) in fluidic contact or out of fluidic contact with a sample loop (which may operate at an atmospheric pressure or the like), very fast and intense pressure pulses may be generated. A compressed mobile phase may therefore be suddenly expanded and beats or even explodes against walls of the valve. This conventionally results in a high wear and abrasion of the valve. By applying a DLC comprising stack coating according to an exemplary embodiment, the surface properties of the valve may be significantly improved.

A bush bearing may be formed by two frictional partners. Such a stack coating of an adhesion-promoting layer and DLC may be further refined by performing an ion implantation in a surface of the DLC layer. This may be accomplished by CVD (chemical vapor deposition) or PECVD (plasma enhanced chemical vapor deposition). For example, a plasma carbon substance may be directed onto a surface of the respective shear valve member. By using a plasma method, it is possible to use both an electrically conductive or an electrically insulating substrate. By adjusting a number or an amount of ions and/or a voltage applied for such a plasma process, a depth of penetration of the ions may be adjusted, and therefore the surface property of the DLC comprising stack.

In the following, further exemplary embodiments of the method will be explained. However, these embodiments also apply to the shear valve, to the sample injector, and to the fluid separation system.

In an embodiment, the ion implantation layer may be formed by an ion implantation procedure. Ion implantation may be denoted as a material engineering process by which ions of a material can be implanted into another solid, thereby changing the physical properties of the solid. These ions may introduce a chemical change in the target in that they can be a different element than the target and/or a structural change in that the crystal structure of the target can be modified by the implantation. By this ion implantation, a tribological matching between the shear valve members may be achieved or refined.

In an embodiment, a surface of a solid body of the first shear valve member and/or of the second shear valve member may be polished before forming the adhesion-promoting layer. By smoothing the solid body, the formation of the adhesion-promoting layer may be performed in a more reliable manner, i.e. thereby also further improving the adhesion function of the adhesion-promoting layer for a DLC layer. Therefore, a completely planar support surface may be formed.

In an embodiment, a surface of a solid body of the first shear valve member and/or of the second shear valve member may be functionalized before forming the adhesion-promoting layer. For instance, such a functionalization may include a treatment of the surface by a plasma such as an argon plasma. With such a functionalization, a properly activated base may be prepared for the subsequent deposition of the adhesion-promoting layer.

In an embodiment, forming at least a part of the diamond like carbon layer and/or the adhesion-promoting layer may comprise inserting a deposition electrode into a groove of the fluid path and/or in one or more of the ports, wherein the deposition electrode may be configured for providing material forming at least a part of the diamond like carbon layer or the adhesion-promoting layer, respectively. Therefore, small electrode structures may be locally inserted into ports, groove, etc. of the shear valve members to locally deposit material on a surface for the formation of a protection against cavitation effects or the like.

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

Figure 1:
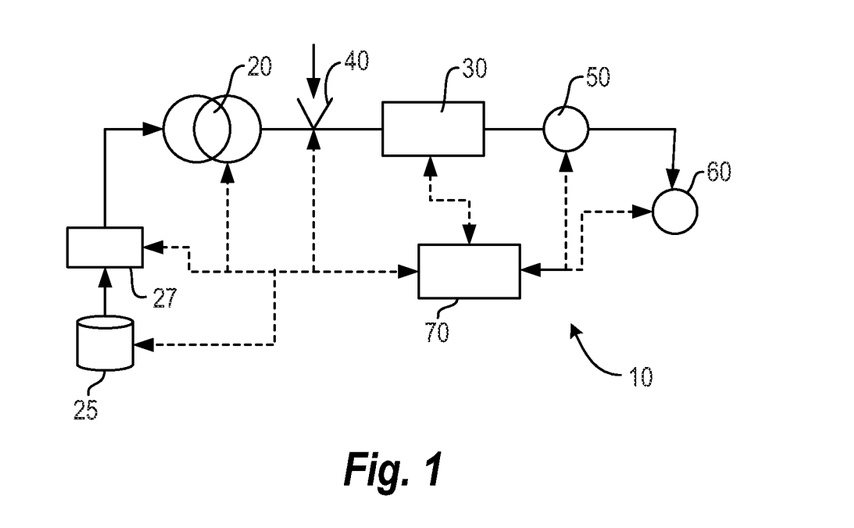
FIG. 1 shows a liquid separation system 10, in accordance with embodiments of the present invention, e.g. used in high performance liquid chromatography (HPLC).

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a sample fluid into the mobile phase. The stationary phase of the separating device 30 is adapted for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g.

controlling sample injection or synchronization sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provides data back.

Figure 2:
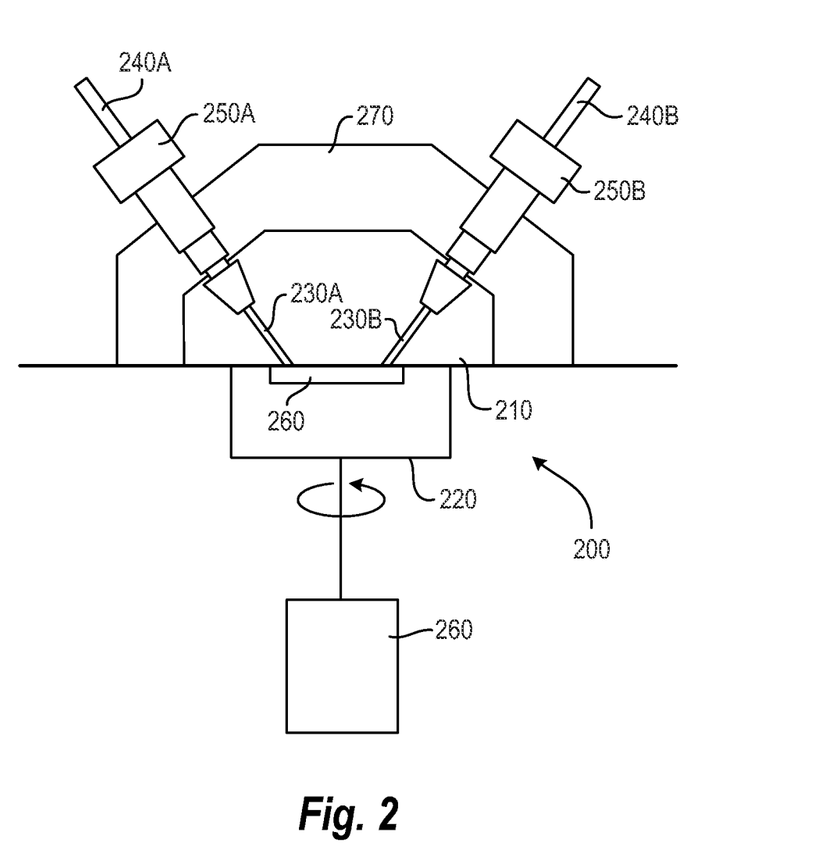
FIG. 2 shows an exemplary embodiment of a shear valve 200 according to the present invention.

FIG. 2 shows an exemplary embodiment of a shear valve 200 according to the present invention, which might be used in the liquid separation system 10 as depicted in FIG. 1. The shear valve 200 comprises a first shear valve member 210 as a stator, and a second shear valve member 220 as a rotor. By rotating the second shear valve member 220, the first and second shear valve member 210 and 220 can be moved with respect to each other. The first shear valve member 210 comprises a plurality of ports 230, with ports 230A and 230B exemplarily shown in FIG. 2. A fluid conduit 240 such as a capillary, e.g. a glass or metal capillary, can be coupled to each port 230 respectively. In FIG. 2, a capillary 240A is coupled via a fitting 250A to the port 230A, and a capillary 240B is coupled via fitting 250B to the port 230B.

The second shear valve member 220 (rotor) comprises a fluid path 260. Dependent on a relative movement position of the first and second shear valve members 210 and 220, the fluid path 260 can be moved to couple between respective ones of the ports 230. In the exemplary illustration of FIG. 2, the fluid path 260 is shown in a position to couple between the ports 230A and 230B, thus allowing a fluid connection between the capillary 240A and 240B. By rotating (as indicated by the curved arrow in FIG. 2) the second shear valve member 220, ports 230A and 230B can be decoupled from each other, thus intermitting the fluid connection between the capillary 240A and 240B. This will also be seen in more detail in FIG. 3.

The rotor of the second shear valve member 220 is preferably moved by a drive 260, such as a motor, but might also be moved (alternatively or in addition) by manual operation. The first shear valve member 210 is at least partly coated with a multi-layer diamond like carbon (DLC) stack comprising TiN as an adhesion-promoting layer and DLC as a hardening layer. The material of the second shear valve member is preferably selected to be tribologically matching to the multi-layer DLC stack material of the first shear valve member. In the embodiment of FIG. 2, the first shear valve member 210 is a solid material body of multi-layer DLC stack, while the second shear valve member 220 is embodied by the same multi-layer DLC stack as well.

In the embodiment of FIG. 2, the first shear valve member 210 is housed by a housing 270, which has been fitted to the first shear valve member 210 preferably by using a shrinking process. The housing 270 thus allows pre-stressing against the first shear valve member 210 to reduce tension in the first shear valve member 210. The housing 270 can be made of a stainless steel, which might also be coated with TiN as an adhesion-promoting layer and DLC applied thereon.

Figure 3:
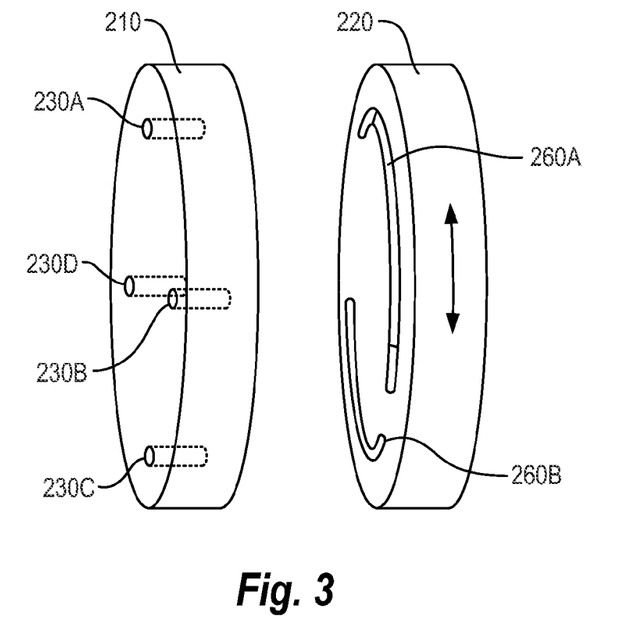
FIG. 3 shows the first and second shear valve members 210 and 220 in a three dimensional view.

FIG. 3 shows the first and second shear valve members 210 and 220 in a three dimensional and enlarged view. In this embodiment, the valve 200 shall be a 2/4 valve, i.e. a valve having two fluid paths 260A and 260B and four ports 230A, 230B, 230c and 230D. By rotating the second shear valve member 220 (as indicated by the arrow), neighboring ones of the ports 260 can be coupled to each other via a respective one of the fluid paths 260A and 260B, as well known in the art and also disclosed by the documents cited in the introductory part of the description.

Figure 4:
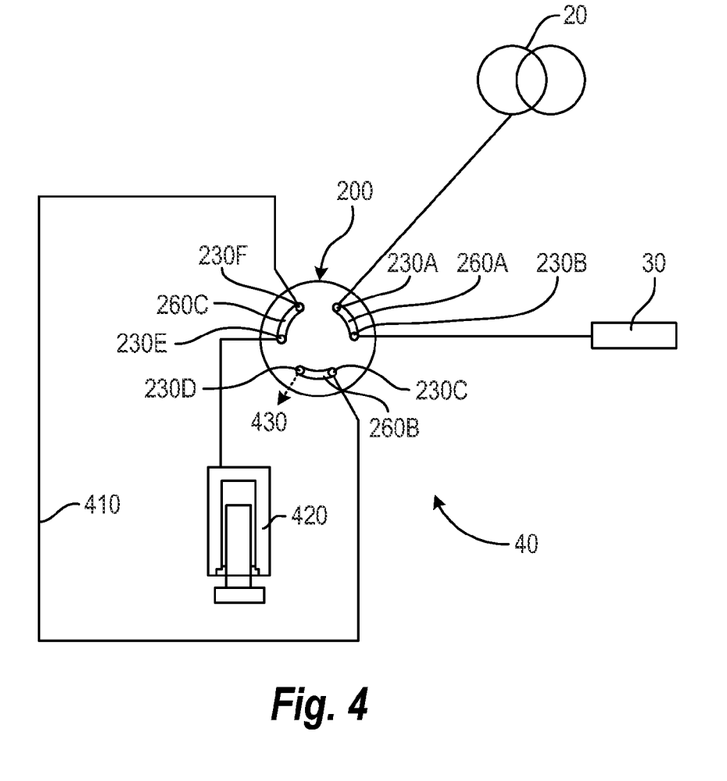
FIG. 4 shows an embodiment of the shear valve 200 in the sample injector 40 of FIG. 1.

FIG. 4 shows an embodiment of the shear valve 200 in the sample injector 40 (see FIG. 1). The shear valve is embodied here as a 3/6 valve, i.e. having three fluid paths and six ports. The injector 40 comprises a sample loop 410, which can be filled via a pump 420 (e.g. a syringe) from any kind of source (e.g. a vessel, vial, bottle, syringe, pump, metering device) generally symbolized here by arrow 430.

The shear valve 200 in the example of FIG. 4 is a 3/6 valve with three fluid paths 260A, 260B and 260C and six ports 230A-230F. In the position as indicated in FIG. 4, the pump 20 is coupled directly via ports 230A and 230B and fluid path 260A to column 30. In this state, the syringe 420 can load sample fluid e.g. from a vessel (symbolized by reference no. 430) into the sample loop 410.

By turning the fluid paths 260A-260C (clockwise or anti-clockwise) to the next neighboring port 230, the pump 20 is now coupled via the fluid path 260C and the ports 230A and 230F to the sample loop 410, and again via the fluid path 260A and the ports 230C and 230B to the column 30. In this state the sample loop 410 is now coupled between the pump 20 and the column 30 for injecting any sample fluid contained in the sample loop 410 into the mobile phase, so that compounds of the sample fluid can be separated whilst propagating through the column 30. Rotating the rotor 220 into the (next) neighboring position will lead to the state as shown in FIG. 4.

It is clear that beyond or instead of the shear valve 220 being embodied as a sample injecting valve as shown in FIG. 4, the shear valve 200 may also be used in any other suitable position in the fluid separation system 10 (as depicted in principle in FIG. 1). For example, the shear valve 200 can be provided as a high pressure purge valve for the pump 20, which is usually embodied as a positive displacement pump. Alternatively or in addition, the shear valve 20 might also be used as a flow path switching valve anywhere in the system 10 for switching from one flow path to another flow path, e.g. at a column oven, etc.

In the following, referring to FIG. 5 to FIG. 10, a method of manufacturing a shear valve for use in a HPLC as shown in FIG. 1 according to an exemplary embodiment of the invention will be explained.

Figure 5:
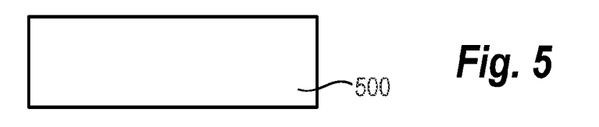
FIG. 5 to FIG. 10 show layer sequences obtained during performing a method of manufacturing a shear valve according to an exemplary embodiment.

FIG. 5 schematically shows a solid body 500 forming at least part of a shear valve member, wherein an upper surface of the solid body 500 may be processed with grooves and/or ports (not shown) to enable a fluid communication between two cooperating frictional partners, as shown in FIG. 2 to FIG. 4.

Figure 6:
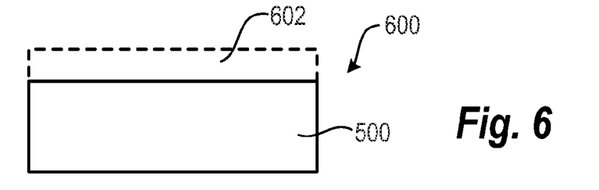

In order to obtain a layer sequence 600 shown in FIG. 6, the solid body 500 made of a hardened steel material such as super duplex steel may be polished at an upper surface 602 so as to smoothen this surface 602 by removing any surface topology.

Figure 7:
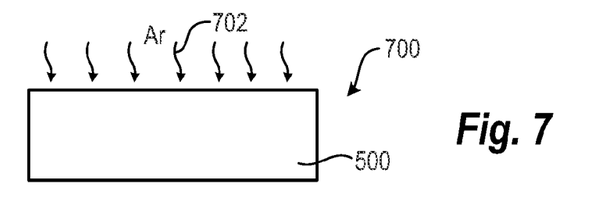

In order to obtain a layer sequence 700 shown in FIG. 7, the polished layer sequence 600 or alternatively the original solid body 500 may be made subject of an argon plasma function-alization procedure. By treating the upper surface of the layer sequence 600 in an argon plasma atmosphere, as indicated schematically by reference numeral 702, the upper surface of the solid body 500 is prepared in an optimum manner for a subsequent deposition of a multilayer DLC stack. By the functionalization as shown in FIG. 7, a surface of the steel body 500 is activated by argon etching.

Figure 8:
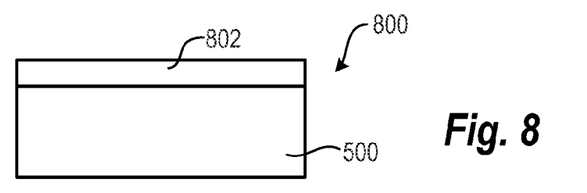

In order to obtain a layer sequence 800 shown in FIG. 8, the layer sequence 700 or alternatively the layer sequence 600 or alternatively the pure solid body 500 may be made subject of a deposition procedure during which a 3 µm thick titanium nitride layer 802 is formed as an adhesion-promoting layer as a support for a subsequent DLC deposition. Such a titanium nitride layer may be manufactured in a vacuum oven. The adhesion-promoting layer 802 improves the hardness and provides a proper bonding between the steel body 500 and a subsequently formed DLC layer.

Figure 9:
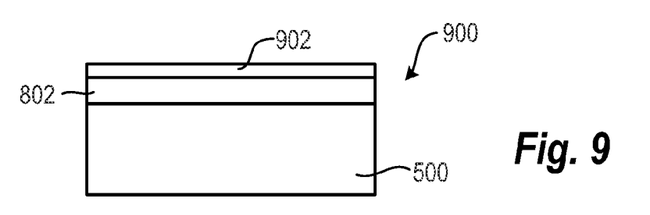

As shown as a layer sequence 900 in FIG. 9, a diamond like carbon (DLC) structure 902 with a thickness of 1 µm is formed directly on the adhesion-promoting layer 802. In the shown embodiment, the DLC layer 902 is formed "in process", i.e. in the vacuum oven which has also been used for depositing the titanium nitride layer 802.

Figure 10:
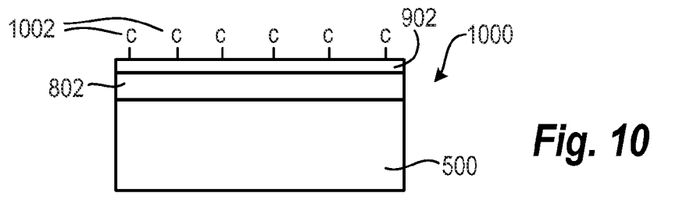

The multilayer DLC stack 802, 902 may then be made subject of an ion implantation treatment, as shown in a layer sequence 1000 in FIG. 10. With such a plasma carbon treatment, carbon ions 1002 are formed on an upper surface of the DLC layer 902.

It has turned out to be highly appropriate to provide such a layer sequence 802, 902, 1002 as a multi-stack DLC comprising coating on both shear valve members cooperating as frictional partners in a tribologically matching manner so that the two shear valve members act as a tribological pair.

Optionally, a further titanium layer for further improving the adhesion between the steel 500 material and the DLC 902 material may be provided. It is possible to deposit a further titan layer (for instance with a thickness of 1 µm). The ion implanted carbon layer 1002 which may also be substituted by $MoS_2$ may reduce the static friction/dynamic friction and may therefore promote a low frictional sliding of the friction partners contacting one another.

Particularly the DLC layer 902 serves as a wear-free hardening layer. The adhesion-promoting layer 802 may even have non-ideal frictional properties when taken alone. According to an embodiment, this function may be fulfilled by the DLC layer 902 covering the adhesion-promoting layer 802. The adhesion-promoting layer 802 serves as a bonding agent or coupling agent and also contributes to the high mechanical robustness of the layer sequence 1000.

Figure 11:
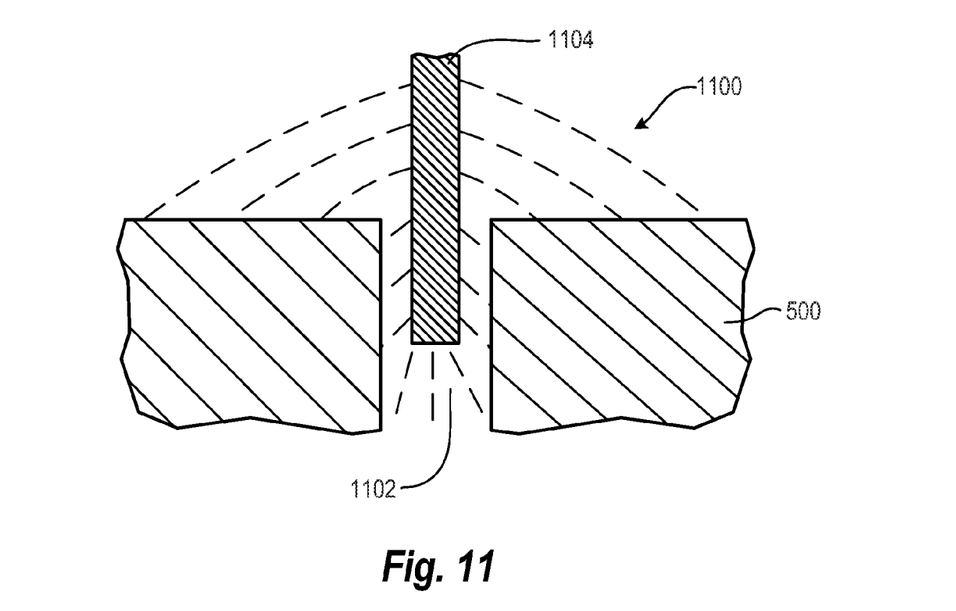
FIG. 11 and FIG. 12 illustrate formation of a stacked coating in a groove and in a port, respectively, using a deposition electrode according to an exemplary embodiment.

FIG. 11 shows an arrangement 1100 of a shear valve member having a port 1102 as part of a fluidic channel. In order to cover even an inner surface of the port 1102 with a DLC multi-stack layer, an electrode 1104 may be inserted into the port 1102, and material of the electrode 1104 may be deposited on an inner surface of the port 1102.

Figure 12:
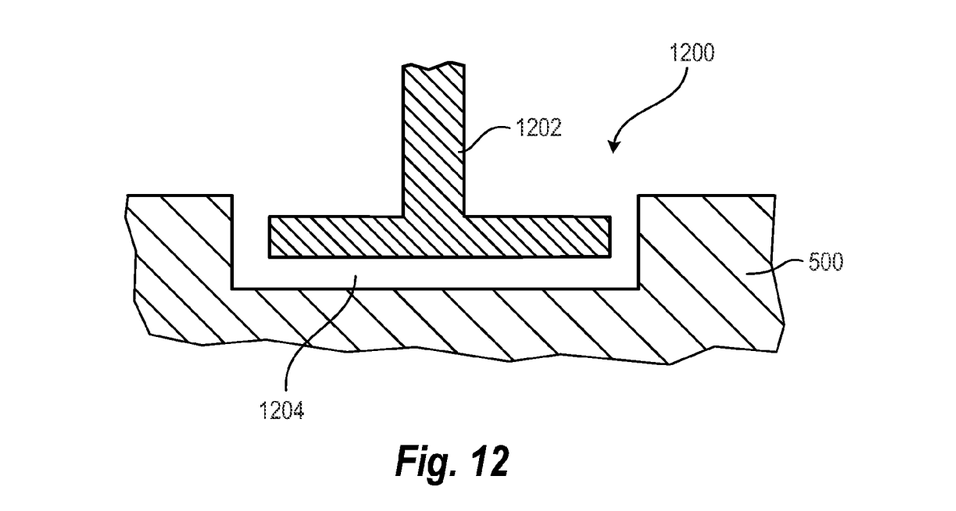

In a similar manner, as shown in FIG. 12, a correspondingly shaped auxiliary electrode 1202 may be inserted into a groove 1204 of a shear valve member 1200 so as to deposit material for a multi-stack DLC layer directly on an inner surface of the groove 1204.

For instance, the shear valve member 1100 may serve as a stator, and the shear valve member 1200 may serve as a rotor of a rotary valve in which a fluid communication between the port 1102 and the groove 1204 can be selectively enabled or disabled, depending on the switching state of the valve.

For instance, in a procedure of manufacturing a shear valve member, 1.5434 steel as a support material may be used. In order to improve the protection against cavitation by a multilayer system, the steel substrate may be polished (for instance with a roughness of 0.1 μm) and may be hardened before further processing. The surface may be further be cleaned, for instance by putting the solid body in a basket and by immersing the solid body in a cleaning solution.

Subsequently, a multilayer coating may be formed using a PVD method (plasma enhanced chemical vapor deposition). In this context, an argon ion etching procedure may be performed with a voltage of 600 V and a current of 10 A for 15 minutes. Subsequently, a 3 μm thick titanium nitride layer may be deposited with a procedural time of 40 minutes. Subsequently, a DLC layer (IBAD-DLC) may be formed with a thickness of 1 μm with a procedural time of 20 minutes. Then, the layer sequence may be made subject of an ion treatment for 30 minutes so that an $MoS_2$ layer is formed.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A shear valve for use in a high performance liquid chromatography system, the shear valve comprising:
   a first shear valve member and a second shear valve member, wherein at least one of the first and second shear valve members is adapted to be moved with respect to the other, one of the first and second shear valve members comprises a plurality of ports, and the other comprises at least one fluid path for fluidly coupling respective ones of the ports in dependency on a relative movement position of the first and second shear valve members with respect to each other,
   wherein the first shear valve member is at least partially coated with an adhesion-promoting layer and a diamond like carbon layer on the adhesion-promoting layer and an ion implantation layer on the diamond like carbon layer.

2. The shear valve of claim 1, wherein the ion implantation layer comprises one of the group consisting of carbon, molybdenum disulfide, titanium, titaniumdioxide, and boronitride.

3. The shear valve of claim 1, wherein the first shear valve member comprises a first solid body on which the adhesion-promoting layer and the diamond like carbon layer are arranged.

4. The shear valve of claim 3, wherein the first solid body comprises at least one of the group consisting of steel, stainless steel, duplex steel, super duplex steel, steel with a manganese contribution of at least 3%, steel with a manganese contribution of at least 5%, steel with a nickel contribution of less than 8%, steel with a nickel contribution of less than or equal to 5%, and an electrically conductive material.

5. The shear valve of claim 1, wherein the second shear valve member is at least partially coated with a further adhesion-promoting layer and a further diamond like carbon layer on the further adhesion-promoting layer.

6. The shear valve of claim 5, comprising at least one of:
   the second shear valve member comprises a second solid body on which the further adhesion-promoting layer and the further diamond like carbon layer are arranged;
   the second solid body comprises at least one of the group consisting of steel, stainless steel, duplex steel, super duplex steel, steel with a manganese contribution of at least 3%, steel with a manganese contribution of at least 5%, steel with a nickel contribution of less than 8%, steel with a nickel contribution of less than or equal to 5%, and an electrically conductive material.

7. The shear valve of claim 1, wherein the second shear valve member comprises a second solid body on which a further ion implantation layer is arranged.

8. The shear valve of claim 7, comprising at least one of:
   the second solid body comprises at least one of a polymer material, polyimide, polyamideimide, polyetheretherketone, PEEK, a PEEK Blend T-Series, a PEEK/PBI/PTFE Blend, a PEEK-HT/PBI/Carbon/PTFE Blend, a PEEK-HT/PBI/Carbon/$TIO_2$/PTFE Blend, a metal, and a ceramics;
   the further ion implantation layer comprises at least one of the group consisting of carbon, molybdenum disulfide, titanium, and titanium oxide.

9. The shear valve of claim 1, comprising a housing for housing one of the first and the second shear valve members, wherein the housing is prestressed against the housed shear valve member.

10. The shear valve of claim 9, wherein the first shear valve member is the housed shear valve member.

11. The shear valve of claim 1, wherein the fluid path comprises a groove.

12. The shear valve of claim 11, comprising at least one of:
    the groove is delimited by at least one of an insert, a ceramic insert, and a molded ceramic insert;
    at least a part of the diamond like carbon layer and the adhesion-promoting layer covers at least a part of a surface delimiting the groove.

13. The shear valve of claim 1, comprising at least one of:
    the diamond like carbon layer has a thickness in range between 0.2 μm and 3 μm;
    the adhesion-promoting layer comprises one of the group consisting of titanium nitride and a cobalt compound;
    the adhesion-promoting layer has a thickness in range between 1 μm and 5 μm;
    the shear valve comprises an ion implantation layer on the diamond like carbon layer;
    the shear valve is a rotary valve, and the first and the second shear valve members are rotatably movable with respect to each other;
    the shear valve is a translational valve, and the first and the second shear valve members are translationally movable with respect to each other;
    the second shear valve member is at least partially coated with or comprised of a material tribologically matching to the first shear valve member;
    at least a part of the diamond like carbon layer and the adhesion-promoting layer covers at least a part of a surface within one or more of the ports;
    one or more of the ports comprise a through hole having an opening fluidly coupling with the fluid path dependent on the moving position;
    the first shear valve member comprises the plurality of ports, and the second shear valve member comprises the at least one fluid path for fluidly coupling respective ones of the ports of the first shear valve member in dependency on a relative movement position of the first and second shear valve members with respect to each other;
    the second shear valve member comprises the plurality of ports, and the first shear valve member comprises the at least one fluid path for fluidly coupling respective ones of the ports of the second shear valve member in dependency on a relative movement position of the first and second shear valve members with respect to each other;

the second shear valve member is adapted to be moved with respect to the first shear valve member;

the shear valve comprises a drive for moving the one of the first and second shear valve members to be moved;

the shear valve comprises a valve control unit adapted for controlling a movement of the first and second shear valve members with respect to each other;

the shear valve is adapted to conduct a liquid in the at least one fluid path at a high pressure at which compressibility of the liquid becomes noticeable;

the shear valve is adapted to conduct a liquid in the at least one fluid path at a high pressure in a range of 20-200 MPa.

14. The shear valve of claim 1, wherein the shear valve is one of:

a sample injection valve for injecting a liquid sample into a high pressure flowing stream of liquid;

a high-pressure purge valve for a positive displacement pump;

a flow path switching valve for switching from one flow path to another flow path.

15. A sample injector adapted to introduce a sample fluid into a mobile phase, wherein the mobile phase is to be driven by a mobile phase drive through a separation unit for separating compounds of the sample fluid in the mobile phase, the sample injector comprising:

a sample loop for receiving the sample fluid, a shear valve of claim 1 for switching the sample loop between the mobile phase drive and the separation unit.

16. A fluid separation system for separating compounds of a sample fluid in a mobile phase, the fluid separation system comprising:

a mobile phase drive, particularly a pumping system, adapted to drive the mobile phase through the fluid separation system, a separation unit, particularly a chromatographic column, adapted for separating compounds of the sample fluid in the mobile phase, and a shear valve of claim 1 for switching from one flow path to another flow path within a fluid separation flow path between the mobile phase drive and the separation unit.

17. The fluid separation system of claim 16, further comprising at least one of:

a sample injector adapted to introduce the sample fluid into the mobile phase;

a detector adapted to detect separated compounds of the sample fluid;

a collection unit adapted to collect separated compounds of the sample fluid;

a data processing unit adapted to process data received from the fluid separation system;

a degassing apparatus for degassing the mobile phase.

18. A method of manufacturing a shear valve for use in a high performance liquid chromatography system, the method comprising:

assembling a first shear valve member and a second shear valve member so that at least one of the first and second shear valve members is adapted to be movable with respect to the other, one of the first and second shear valve members comprises a plurality of ports, and the other comprises at least one fluid path for fluidly coupling respective ones of the ports in dependency on a relative movement position of the first and second shear valve members with respect to each other, at least partially coating the first shear valve member with an adhesion-promoting layer and a diamond like carbon layer on the adhesion-promoting layer and an ion implantation layer on the diamond like carbon layer.

19. The method of claim 18, comprising at least one of:

forming an ion implantation layer on the diamond like carbon layer by ion implantation;

forming an ion implantation layer on the diamond like carbon layer by ion implantation, wherein the ion implantation layer is formed by one of the group consisting of a plasma treatment of the diamond like carbon layer, chemical vapour deposition, and plasma-enhanced chemical vapour deposition;

polishing, particularly electropolishing or mechanically polishing, a surface of a solid body of the first shear valve member before forming the adhesion-promoting layer on the polished surface of the solid body;

functionalizing a surface of a solid body of the first shear valve member before forming the adhesion-promoting layer on the functionalized surface of the solid body;

functionalizing a surface of a solid body of the first shear valve member before forming the adhesion-promoting layer on the functionalized surface of the solid body, wherein the functionalizing comprises a treatment of the surface by a plasma, particularly by an argon plasma;

wherein forming at least a part of the diamond like carbon layer and the adhesion-promoting layer comprises inserting a deposition electrode into at least one of a groove of the fluid path and one or more of the ports, the deposition electrode being configured for providing a substance forming at least the part of the diamond like carbon layer and the adhesion-promoting layer in the at least one of the groove and the one or more of the ports.

* * * * *